United States Patent
Doyle et al.

(10) Patent No.: US 8,907,286 B2
(45) Date of Patent: Dec. 9, 2014

(54) GAS PHASE COOLING AND MIXTURE ANALYSIS

(75) Inventors: John M. Doyle, Belmont, MA (US); David S. Patterson, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 138 days.

(21) Appl. No.: 13/640,225

(22) PCT Filed: Apr. 12, 2011

(86) PCT No.: PCT/US2011/032042
§ 371 (c)(1),
(2), (4) Date: Jan. 18, 2013

(87) PCT Pub. No.: WO2011/130215
PCT Pub. Date: Oct. 20, 2011

(65) Prior Publication Data
US 2013/0107244 A1    May 2, 2013

Related U.S. Application Data

(60) Provisional application No. 61/323,101, filed on Apr. 12, 2010.

(51) Int. Cl.
*G01N 21/64* (2006.01)
*G01N 22/00* (2006.01)
*G01N 21/25* (2006.01)

(52) U.S. Cl.
CPC .............. *G01N 21/255* (2013.01); *G01N 21/64* (2013.01); *G01N 22/00* (2013.01); *G01N 2021/6417* (2013.01); *G01N 21/6402* (2013.01); *G01N 2021/6473* (2013.01)
USPC ........................................ 250/343; 250/458.1

(58) Field of Classification Search
CPC .............. G01N 2021/1761; G01N 2021/3595; G01N 21/00; G01N 21/17; G01N 21/1717; G01N 21/35; G01N 21/3504; G01N 22/00
USPC .......... 250/339.12, 339.13, 343, 458.1, 459.1
See application file for complete search history.

(56) References Cited

PUBLICATIONS

Patterson, David et al., "Intense atomic and molecular beams via neon buffer-gas cooling", New Journal of Physics, vol. 11, No. 5, May 2009.*
International Search Report and Written Opinion corresponding to International Application No. PCT/US2011/032042, mailed Aug. 18, 2011.
Egorov D. et al., "Buffer-gas Cooling of Atomic and Molecular Beams", Physical Review A, 66, (2002) pp. 043401-1-043401-8.
Hatakeyama A., et al., "Atomic Alkali-metal Gas Cells at Liquid-Helium Temperatures: Loading by Light-induced Atom Desorption", Physical Review A, 65, (2002) pp. 022904-1-022904-9.

* cited by examiner

*Primary Examiner* — Mark R Gaworecki
(74) *Attorney, Agent, or Firm* — Foley & Lardner LLP

(57) ABSTRACT

A system includes a cold cell tube configured to receive a mixture of a target gas and a buffer gas to cool the target gas to a temperature at which a partial pressure of the target gas is greater than the saturated vapor pressure of the target gas while maintaining at least a portion of the target gas in the gas phase. The system also includes a spectroscopic module configured to detect the cooled target gas in the cold cell tube; and an analysis module configured to determine a characteristic of the target gas based on the results of the detecting.

31 Claims, 9 Drawing Sheets

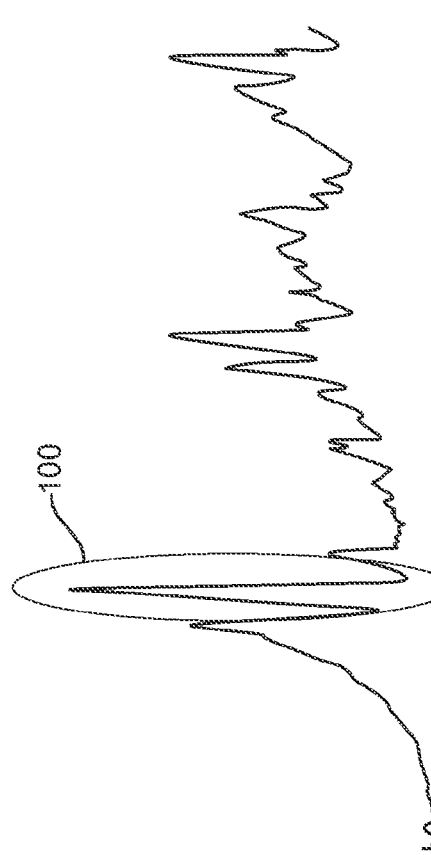
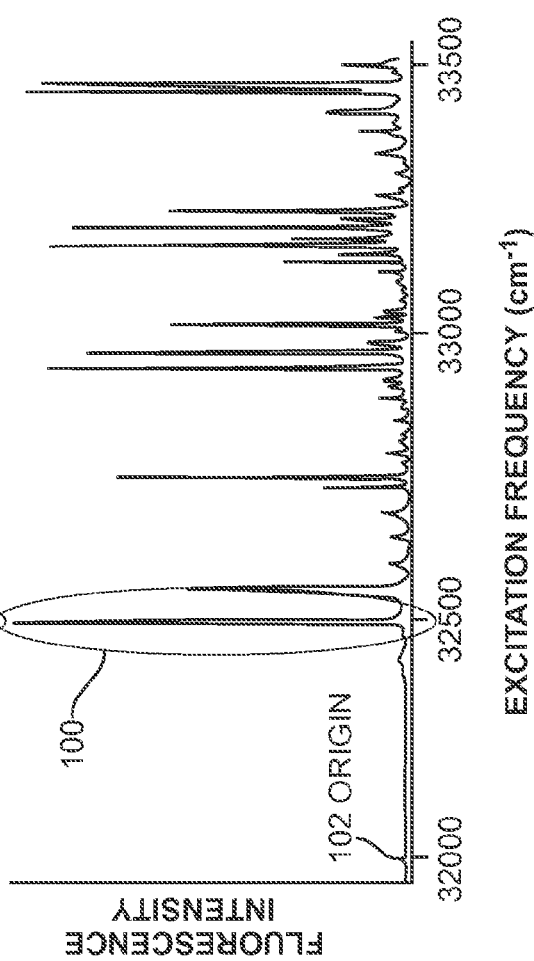
FIG. 1A (PRIOR ART)
FIG. 1B (PRIOR ART)

US 8,907,286 B2

GAS PHASE COOLING AND MIXTURE ANALYSIS

CROSS-REFERENCE TO RELATED APPLICATIONS

This application is the National Stage of International Application No. PCT/US2011/032042 filed on Apr. 12, 2011, which claims the benefit of the priority date of U.S. Provisional Application No. 61/323,101, filed on Apr. 12, 2010. The contents of these applications are hereby incorporated by reference in its entirety.

BACKGROUND

The accurate and sensitive analysis of complicated gas mixtures has many applications in industry, process control, forensics, pharmacology, medicine, and environmental science.

Mixture analysis is also an essential tool in biological, chemical, and physics research. Examples of unsolved, or imperfectly solved, problems are easy to find: over 1000 compounds are known to exist in human breath, including compounds which are markers of health risks, cancer, and environmental hazards; a wide variety of organic amines and carboxylic acids, present in nanomolar concentrations in seawater, are important intermediates in decomposition processes and provide a quantitative measure of marine ecosystem metabolic cycles; the pheromones of butterflies and moths include at least hundreds of different compounds, many of them isomers differing only by the position of a double bond; and human blood and urine contain at least dozens and likely hundreds of biologically important hormones.

Complex gas mixtures are generally analyzed using ion mobility spectrometry, gas chromatography (GC), and gas chromatography mass spectrometry (GC/MS). In gas chromatography, a gas sample to be analyzed is mixed with an inert carrier gas, such as helium or nitrogen, and flowed through a capillary containing a liquid or polymer coated substrate. Different contaminants elute at different times, effectively sorting the contaminants by time as they exit the end of the capillary column. GC alone can resolve a mixture component with a fraction as low as $10^{-9}$ (parts per billion range) in specialized cases, but generally operates in the $10^{-6}$ range or lower. For complex mixtures, GC is often combined with mass spectrometry (GC/MS) to further resolve mixture components. In this case, molecules are ionized as they elute from the GC column and the ions are detected by a mass spectrometer; the combination of elution time and charge-to-mass ratio can be used to uniquely identify the mixture component. Ion mobility spectrometry, in which a sample is ionized and then allowed to drift through a stationary gas in an electric field, is significantly more sensitive, and is the industry standard when there are a small number of very dilute targets of interest (e.g., for bomb sniffing applications). However, ion mobility spectroscopy is not generally well suited to resolving complex mixtures. In general, gas mixture analysis techniques operate at or near the $10^{-9}$ level, although sensitivities as low as $10^{-12}$ have been achieved for a few specific molecules.

UV spectroscopy of room temperature or warmer gas-phase samples is generally ineffective at resolving complex mixtures. Both absorption and emission spectra are composed of hundreds or thousands of unresolved rotational lines for each vibrational line. In many cases, this broad manifold of lines overlaps with nearby vibrational manifolds; in the case of a mixture, these broad features generally overlap with the spectrum of another mixture component. The 'confusion limit,' at which the spectrum of one component of a mixture overlaps with another component, is reached almost immediately.

At lower temperatures, the confusion limit is radically suppressed; rotational manifolds and hot vibrational bands are suppressed and individual rotational lines can often be resolved. Referring to FIG. 1B, narrow features in the 2 K spectrum of a naphthalene gas produced by a seeded supersonic jet are resolvable into many discrete vibrational lines, such as a peak corresponding to the strong $8_0^1$ transition 100 and peak corresponding the weaker $8_0^0$ transition 102. Referring to FIG. 1A, in the 300K spectrum of naphthalene gas, only a few vibronic lines can be resolved, and these features are considerably broader than the corresponding low temperature peaks. For instance, only the $8_0^1$ transition 100 is resolvable, and the peak is significantly broader than the corresponding cold sample peak.

Ultraviolet/visible emissions spectra are similarly simplified at low temperature. Referring to FIG. 1C, at low temperatures (2 K) at least 10 separate vibronic lines of Perylene can be resolved in the emission spectrum (solid line 104). In the warm (290° C.) spectrum (dashed line 106), no vibronic lines can be resolved.

Microwave (rotational) absorption and emission spectroscopy of room temperature gases is generally somewhat ineffective at resolving mixtures containing large molecules (e.g., more than 10 atoms). For smaller molecules, individual rotational lines can typically be resolved, but large molecules at 300 K or above occupy so many rotational states that the rotational lines overlap and become unresolvable. This broadening is compounded when complex mixtures of many cold molecules are studied. Microwave spectra of large molecules are also drastically simplified at low temperature, as many fewer rotational states are occupied.

Samples of cold molecules with atom number higher than five have been produced using seeded supersonic jets, which produce translationally and rotationally cold molecules moving at high velocity (e.g., 300 m/s or higher). The beam produced by a seeded supersonic jet evolves spatially with a rapidly decreasing density as the molecules move farther away from the beam orifice. Seeded supersonic jets have been used for the analysis of unknown gas mixtures, but experimental sensitivity is limited by the low density and high velocity of the target gas. Typical densities in the cold portion of supersonic beams are more than $10^5$ times lower than in the room temperature input stage of the beam. Simply cooling a warm gas-phase mixture is not generally effective; few molecules have significant vapor pressure below 200 K, and the mixture will simply condense into a liquid or a solid. Spectroscopic features of such condensed phases are generally quite broad.

SUMMARY

In a general aspect, a system includes a cold cell tube configured to receive a mixture of a target gas and a buffer gas to cool the target gas to a temperature at which a partial pressure of the target gas is greater than the saturated vapor pressure of the target gas while maintaining at least a portion of the target gas in the gas phase. The system also includes a spectroscopic module configured to detect the cooled target gas in the cold cell tube; and an analysis module configured to determine a characteristic of the target gas based on the results of the detecting.

Embodiments may include one or more of the following.

The target gas includes a plurality of chemical species. The cold cell tube is configured to cool the target gas to a temperature at which a partial pressure of each chemical species is greater than the saturated vapor pressure of that chemical species. The characteristic of the target gas includes an identity of at least one of the chemical species. For at least one of the chemical species included in the target gas, an elastic scattering cross section between a molecule of the at least one chemical species and a molecule of the buffer gas is greater than an elastic scattering cross section between a first molecule of the buffer gas and a second molecule of the buffer gas.

The cold cell tube is configured to increase a phase space density of the target gas. The cold cell tube is configured to cool the target gas to a temperature at which spectroscopic lines of the target gas are resolvable by the spectroscopic module.

The system further includes an input module configured to receive the mixture of the target gas and the buffer gas; and a transition tube disposed between the input module and the cold cell tube. The transition tube is less than about 10 mm in length. The cold cell tube is longer than the transition tube.

The input module is configured to release to the transition tube a first component of the target gas at a different time than a second component of the target gas. The input module includes a capillary gas chromatograph configured to receive the mixture of the target gas and the buffer gas.

The input module includes a cryogenic plate configured to condense at least some components of the target gas. The system further includes a heating element configured to heat the cryogenic plate. When the cryogenic plate is heated, at least some components of the target gas are released to the transition tube.

A density of the target gas in the cold cell tube does not exceed about $10^{12}$ molecules per $cm^3$.

The spectroscopic module includes a light source configured to excite the cooled target gas; and an emissions detector configured to detect a fluorescence emitted by at least one component of the target gas in response to the excitation. The light source includes a tunable laser configured to emit light at a wavelength capable of exciting the fluorescence of at least one component of the target gas. The emissions detector is configured to simultaneously resolve a plurality of wavelengths. The light source includes a light source configured to emit a plurality of wavelengths; and a monochromator. The light source is configured to sequentially emit the plurality of wavelengths.

The spectroscopic module includes a light source configured to excite the cooled target gas; and an emissions detector configured to detect absorption by at least one component of the target gas in response to the excitation. The light source is configured to simultaneously emit the plurality of wavelengths.

The spectroscopic module includes a microwave source configured to excite the cooled target gas; and a microwave detector configured to detect at least one of absorption or emission of microwaves by at least one component of the target gas in response to the excitation.

The spectroscopic module includes a broadband infrared light source configured to excite the cooled target gas and a detector configured to detect an absorption by at least one component of the target gas in response to the excitation according to Fourier Transform Infrared (FTIR) scanning absorption.

The spectroscopic module is configured to detect the cooled target gas before the target gas precipitates in the cold cell tube.

The cold cell tube is configured to cool the target gas to a temperature below 10 K. The buffer gas includes at least one of helium, neon, and hydrogen ($H_2$).

A density of the buffer gas in the cold cell tube is less than about $10^{18}\,cm^{-3}$. The cold cell tube is configured to cool the target gas without substantially changing a density of the target gas. The buffer gas flows through the cold cell tube with a velocity of less than about 2 m/s.

In another general aspect, a method includes receiving a mixture of a target gas and a buffer gas; cooling the target gas to a temperature at which a partial pressure of the target gas is greater than the saturated vapor pressure of the target gas while maintaining at least a portion of the target gas in the gas phase; spectroscopically detecting the cooled target gas; and determining a characteristic of the target gas based on the results of the detecting.

Embodiments may include one or more of the following.

The target gas includes a plurality of different chemical species. Cooling the target gas includes cooling the target gas to a temperature at which a partial pressure of each chemical species is greater than the saturated vapor pressure of that chemical species. Determining a characteristic of the target gas includes identifying at least one of the chemical species. For at least one of the chemical species included in the target gas, an elastic scattering cross section between a molecule of the at least one chemical species and a molecule of the buffer gas is greater than an elastic scattering cross section between a first molecule of the buffer gas and a second molecule of the buffer gas.

Cooling the target gas includes increasing a phase space density of the target gas. Cooling the gas includes cooling the gas to a temperature at which single vibrational lines of the target gas are spectroscopically resolvable.

The method further includes receiving the mixture of the target gas and the buffer gas in an input module. The method further includes receiving the mixture from the input module into a transition tube; and receiving the mixture from the transition tube into a cold cell tube, wherein the target gas is cooled in the cold cell tube. Receiving the mixture in the input module includes receiving the mixture of the target gas and the buffer gas in a capillary gas chromatograph.

The method further includes releasing from the input module a first component of the target gas at a different time than a second component of the target gas. Receiving the mixture in the input module includes condensing at least some components of the target gas on a cryogenic plate. The method further includes heating the cryogenic plate, wherein, when the cryogenic plate is heated, at least some components of the target gas are released.

A density of the cooled target gas does not exceed about $10^{12}$ molecules per $cm^3$.

Spectroscopically detecting the cooled target gas includes optically detecting the cooled target gas. Optically detecting the target gas includes exciting the target gas using a light source; and detecting a fluorescence emitted by at least one component of the target gas in response to the excitation.

Exciting the target gas includes sequentially emitting a plurality of wavelengths. Optically detecting the target gas includes optically detecting the target gas before the target gas precipitates. Optically detecting the target gas includes exciting the target gas using a light source; and detecting an absorption by at least one component of the target gas in response to the excitation. Exciting the target gas includes simultaneously emitting the plurality of wavelengths.

Spectroscopically detecting the cooled target gas includes exciting the target gas using a microwave source; and detecting at least one of absorption or emission of microwaves by at least one component of the target gas in response to the excitation. Spectroscopically detecting the cooled target gas includes detecting the cooled target gas using pulsed Fourier Transform Microwave Spectroscopy.

Cooling the target gas includes cooling the target gas to a temperature below 10 K. Cooling the target gas includes cooling the target gas without substantially changing a density of the target gas.

The buffer gas includes at least one of helium, neon, and hydrogen ($H_2$).

The systems and methods described herein have a number of advantages. In general, samples of large, cold molecules that are substantially at rest in the laboratory frame can be generated efficiently using relatively inexpensive equipment. Cold (e.g., <10 K) gas molecules occupy far fewer rotational states and thus have narrow spectroscopic peaks that enable the resolution of single vibrational modes.

When using, microwave free induction decay spectroscopy (also known as FTMW spectroscopy), the number of spectral lines scales as $T^{-3/2}$ while the radiated power in any given line varies as $T^{-5}$. The radiated power in any given line is dramatically increased at low temperature. The ability to continuously (i.e., duty cycle of 100%) generate cold molecules at high density allows for high sensitivity spectroscopy.

Unknown gas mixtures composed of up to at least 10,000 components at the part per billion level or better can be quickly resolved with high specificity and high sensitivity. Alternatively, less complex mixtures with, for instance, 500-1000 components can be resolved at the part per trillion level or better. A broad range of analyte molecules can be identified, including molecules composed of at least up to 40 atoms and chemically similar isomers, without the need for recalibration for each analyte under investigation.

Other features and advantages of the invention are apparent from the following description and from the claims.

BRIEF DESCRIPTION OF DRAWINGS

FIGS. 1A and 1B show prior art experimental naphthalene spectra taken at 300 K and in a supersonic jet at 2 K, respectively.

DETAILED DESCRIPTION

Cooling and Detection

Figure 1C:
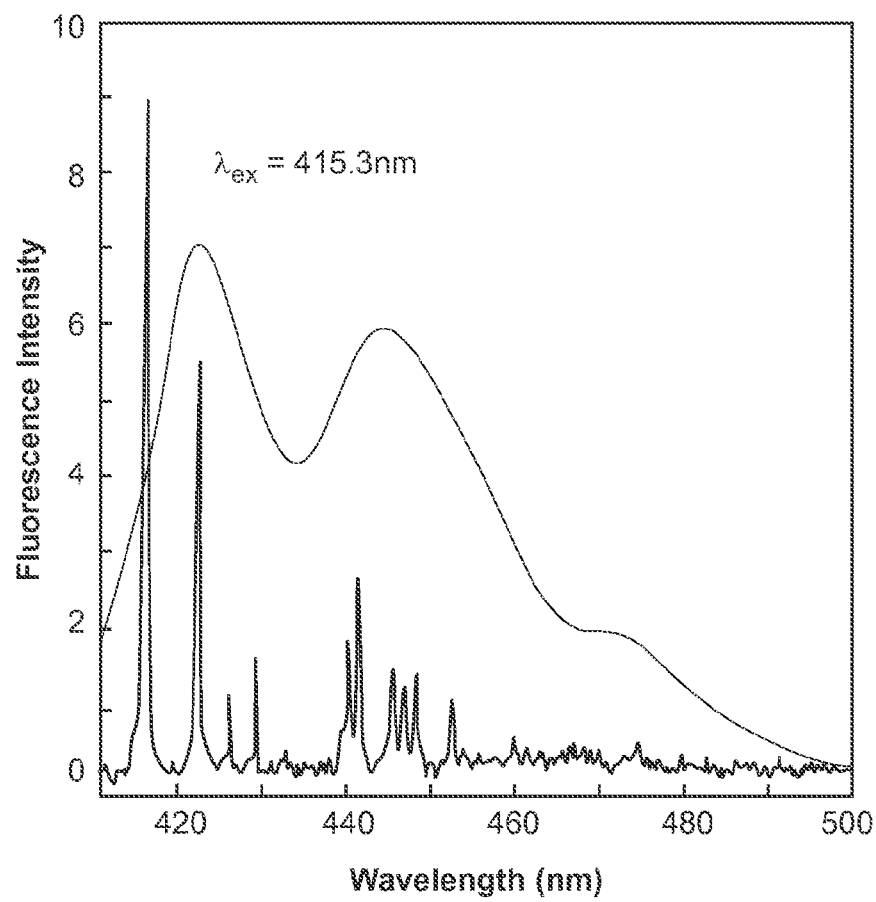
FIG. 1C show prior art experimental perylene spectra taken at 2 K and 290° C.
Figure 2:
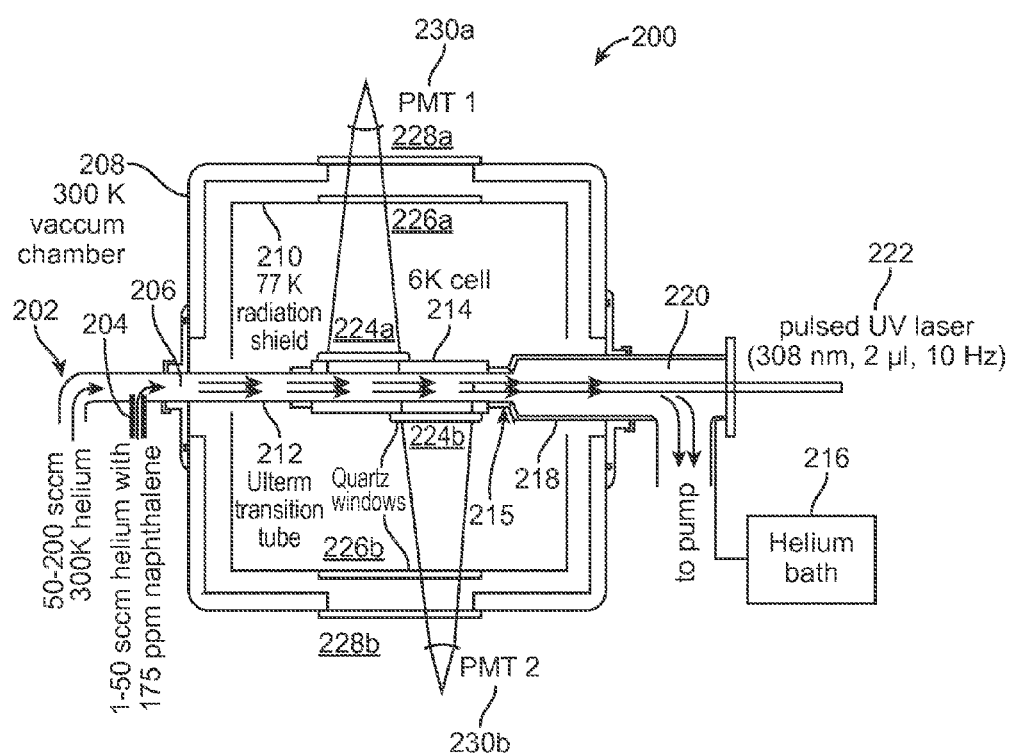
FIG. 2 is a schematic diagram of a direct flow buffer gas cell system for cooling and detecting a gas.

Referring to FIG. 2, a direct flow buffer gas cell 200 allows for the rapid, efficient cooling and detection of gas phase analyte molecules entrained in a helium or neon buffer gas. In particular, a hot (e.g., room temperature) mixture of the analyte molecules and the buffer gas can be rapidly cooled to about 6 K while a substantial fraction of the analyte molecules remain in the gas phase and with a minimal loss of density. These gas phase molecules are slow-moving and exhibit dramatically narrowed absorption and emission peaks compared to room temperature molecules. Although the examples given below demonstrate the cooling and detection of naphthalene ($C_{10}H_8$), the system and methods described herein can be applied to a variety of molecules and mixtures of molecules.

Figure 3:
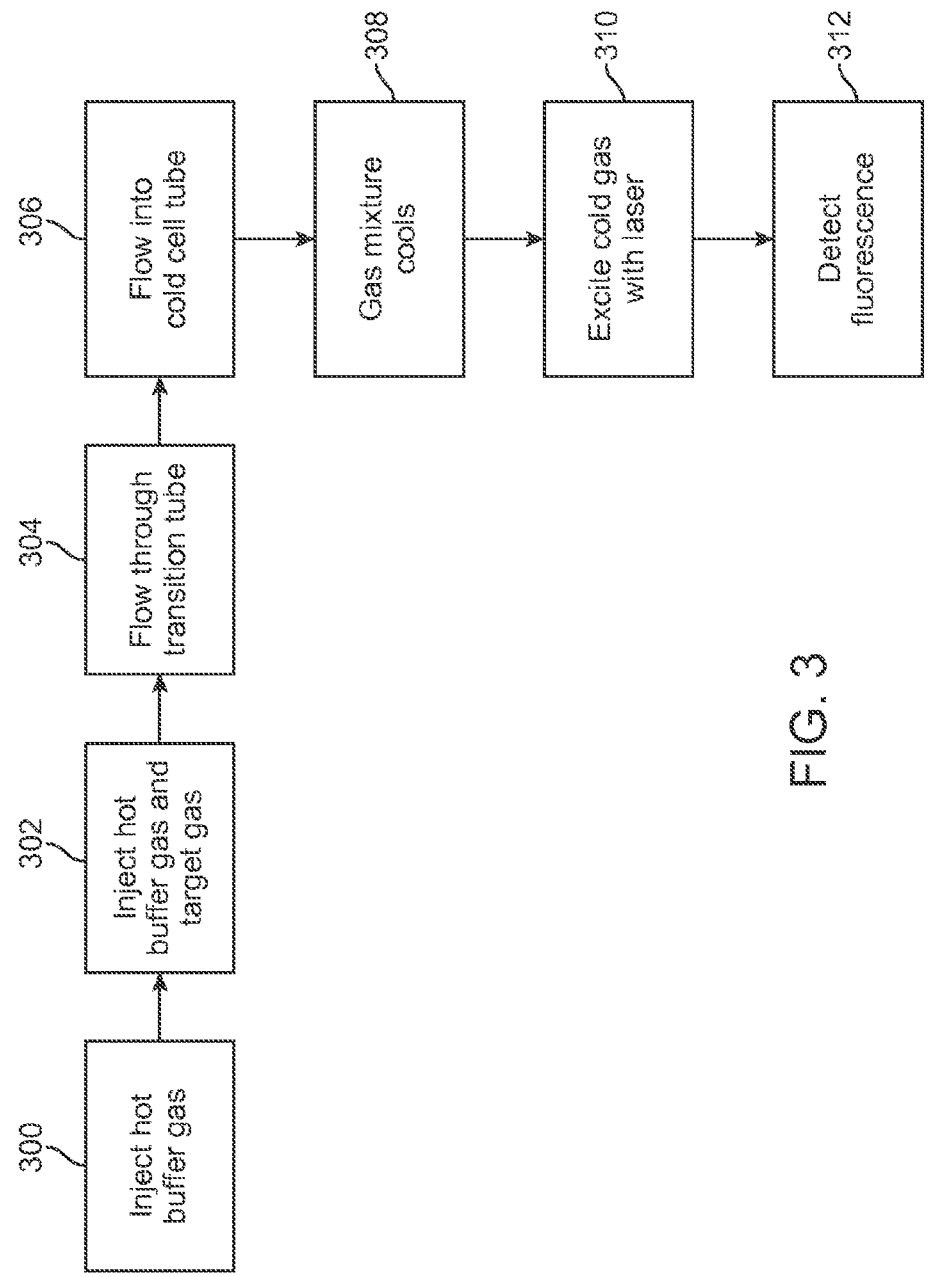
FIG. 3 is a flowchart showing the steps in cooling and detecting a gas in the system of FIG. 2.

Referring to FIGS. 2 and 3, a hot (e.g., 300 K) buffer gas (e.g., helium) is injected into a first input port 202 at a flow rate of between 20-200 sccm (step 300). A hot (e.g., 300 K) mixture of helium buffer gas with 175 parts per million (ppm) of naphthalene is injected into a second input port 204 at a flow rate of between 1-50 sccm (step 302). The helium and naphthalene gas mixture flows through an input tube 206 into a vacuum chamber 208 kept at 300 K, inside of which is a radiation shield 210 kept at 77 K.

The gas mixture flows through a thermally isolating transition tube 212 (step 304) and into a cryogenic cold cell tube 214 (step 306) anchored to a liquid helium bath 216 or a closed cycle cryorefrigerator of a cryostat. Cold cell tube is kept at, e.g., about 6 K. Rapid cooling of the gas mixture is enabled by a short transition tube 212 and by fast flow through buffer gas cell 200 (which in turn is set by the effective pumping speed on the pumping line leaving cold cell tube 214 and by the diameter of the transition tube 212). The length of transition tube 212 is kept as short as possible (e.g., about 1 centimeter long or a few centimeters long) while maintaining an adequate thermal disconnect between input tube 206 and cold cell tube 214. A short transition tube allows gas to pass quickly through the transition tube (e.g., in less than about 0.010 seconds). A short transition tube also reduces input losses and allows low buffer gas flows to be used, leading to lower helium densities in cold cell tube 214. Transition tube 212 is, for instance, a 10 mm long Ultem® tube with a wall thickness of 0.5 mm and a diameter of 1 cm. Cold cell tube 214 is connected to a second transition tube 218 (e.g., an Ultem tube) and into a large (e.g., 2 cm diameter) pumping line 220 capable of supporting a high pumping speed (e.g., at least 80 ft³/min). In order to attain a high flow velocity in transition tube 212, the diameter of the transition tube is smaller than that of pumping line 220.

In general, the 4 K cryogenics of buffer gas cell 200 may be able to withstand a heat load of at most a few watts. Such a low heat load is made possible by a thin-walled transition tube (e.g., about 0.3-0.5 mm) formed of a thermally resistant material (e.g., Ultem®). Transition tube 212 is protected from mechanical stresses, e.g., by connecting the transition tube to cold cell tube 214 via a slightly flexible Teflon sleeve 215. Furthermore, the geometry of transition tube 212 limits thermal blackbody radiation from presenting an unwanted heat load on the cell, e.g., by limiting the diameter of the transition tube to less than about 2 cm. With no buffer gas flowing, the total heat load on the helium bath 216 is about 500 mW, which is likely dominated by black body radiation from the 300 K pumping line 220. With a typical flow of 100 sccm of helium, this heat load increases to about 900 mW. The helium pressure is 2 Torr at input tube 206 and 150 mTorr at the output of the buffer gas cell (i.e., at pumping line 220).

The gas mixture begins to cool as soon as it enters cold cell tube 214 (step 308). Any molecule in the mixture which diffuses to a wall of the cold cell tube sticks and is lost from the gas. As the gas mixture enters the cold cell tube and thermalizes, the phase space density of the naphthalene increases by more than 5 orders of magnitude due to the combination of rotational cooling, translational cooling, and physical compression that occur within cold cell tube 214. The cold naphthalene moves at a flow velocity of about 1.5 m/s and remains in the cold cell tube for about 50 msec. The cold gas mixture in cold cell tube 214 is in thermodynamic equilibrium but is far from thermal equilibrium. In general, a species A (e.g., naphthalene) entrained in the buffer gas will cool in the cold cell tube with little loss as long as the elastic scattering cross section $\sigma_{A-He} > \sigma_{He-He}$. Although the low temperature cross section $\sigma_{N-He}$ for the elastic scattering between naphthalene and helium is not known, the success of the naphthalene experiment described herein indicates that this criterion appears to be met for naphthalene, in agreement with the basic expectation that a naphthalene molecule is physically larger than a helium atom.

Cold gas-phase naphthalene in cold cell tube 214 is detected using laser induced fluorescence, excited by a pulsed UV laser 222 (e.g., 10 Hz, 2 µJ, 308.0 nm) fired along the longitudinal axis of the cold cell tube (step 310). The laser may be tuned along the strong $8_0^1$ transition or the weaker $8_0^0$ origin transition of neutral naphthalene. Naphthalene fluorescence is transmitted through quartz windows 224a, 224b on each side of cold cell tube 214, quartz windows 226a, 226b on each side of radiation shield 210, and quartz windows 228a, 228b on each side of vacuum chamber 208. The fluorescence is collected by photomultiplier tubes (PMTS) 230a, 230b aligned with each series of quartz windows (step 312). PMT 230a collects fluorescence from the upstream half of cold cell tube 214 and PMT 230b collects fluorescence from the downstream half of cold cell tube 214. Comparison of the fluorescence spectra obtained from PMT 230a and PMT 230b allows for direct measurements of loss and cooling as the gas mixture passes through cold cell tube 214.

Figure 4:
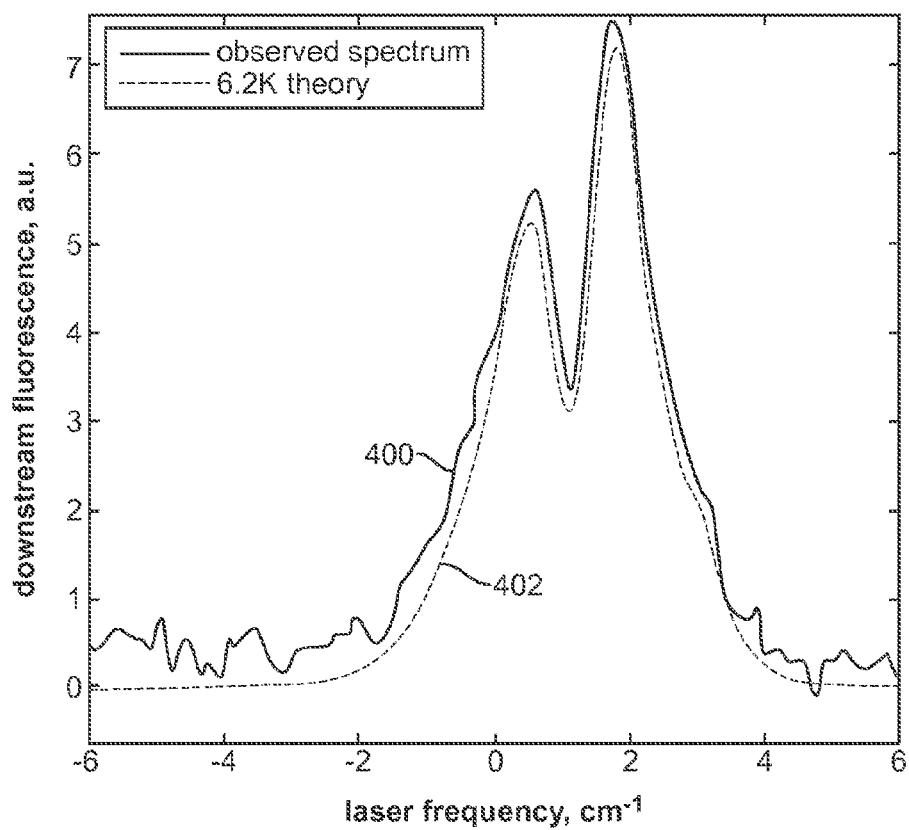
FIG. 4 shows experimental and theoretical fluorescence spectra of naphthalene obtained in the system of FIG. 2.

Referring to FIG. 4, a laser-induced fluorescence (LIF) spectrum of cold naphthalene gas (density $n=2\times10^{11}$ cm$^{-3}$, $T_{cell}=6.2$ K) is shown as a curve 400. A theoretical fit to 6.2 K±1.5 K is shown as a curve 402. Spectrum 400 represents naphthalene which has completely thermalized within the 6 K cold cell. Fluorescence was collected by the downstream PMT tube (230b in FIG. 2), which measures colder gas than the upstream PMT tube. The naphthalene shown in spectrum 400 has cooled from 300 K to 6 K with minimal (less than a factor of 5) loss; that is, about 25% of the input naphthalene remains in the gas phase in this sample. The theoretical spectrum 402 is a sum over hundreds of asymmetrical top rotational lines. Hyperfine structure is ignored but would be undetectable at this resolution. The theory is convolved with a 10 GHz laser linewidth, rendering individual rotational lines invisible.

The absolute density of naphthalene in the cold cell tube is calibrated as follows: under certain, set conditions, the naphthalene loss from one end of the cold cell tube to the other is small. The cold cell tube is longer than the transition tube, and thus the assumption can be made that the loss in the transition tube is also small. The cold density can therefore be estimated using the known input density, and the fluorescence is calibrated using this estimated value. In this particular example, the naphthalene density is known because naphthalene will not accumulate on the walls at 300 K. The helium density is calculated from the pressure, which is bounded by the measured pressures at the input and output of the flow tube. The densities of naphthalene and helium can thus be separated determined through calibrated LIF and direct pressure measurement, respectively.

Under typical conditions, the cold cell tube contains helium at a density of $n_{He}=4\times10^{17}$ cm$^{-3}$ and naphthalene at a density of $n_N=2\times10^{11}$ cm$^{-3}$ at a temperature of 6.2 K. Uncertainties in the understanding of naphthalene loss mechanisms and of the helium pressure within the cold cell tube limit the certainty of the absolute naphthalene density measurement to an order of magnitude. The cold naphthalene is entrained in the moving helium flow, with flow velocity $v\approx1.5$ m/s, compared to a microscopic thermal velocity $c=\sqrt{2k_bT/m}=30$ m/s and typical seeded supersonic beam velocities of greater than 300 m/s. The LIF spectrum 400 thus represents $n_N$ molecules which are effectively at rest in the laboratory frame.

Figure 8:
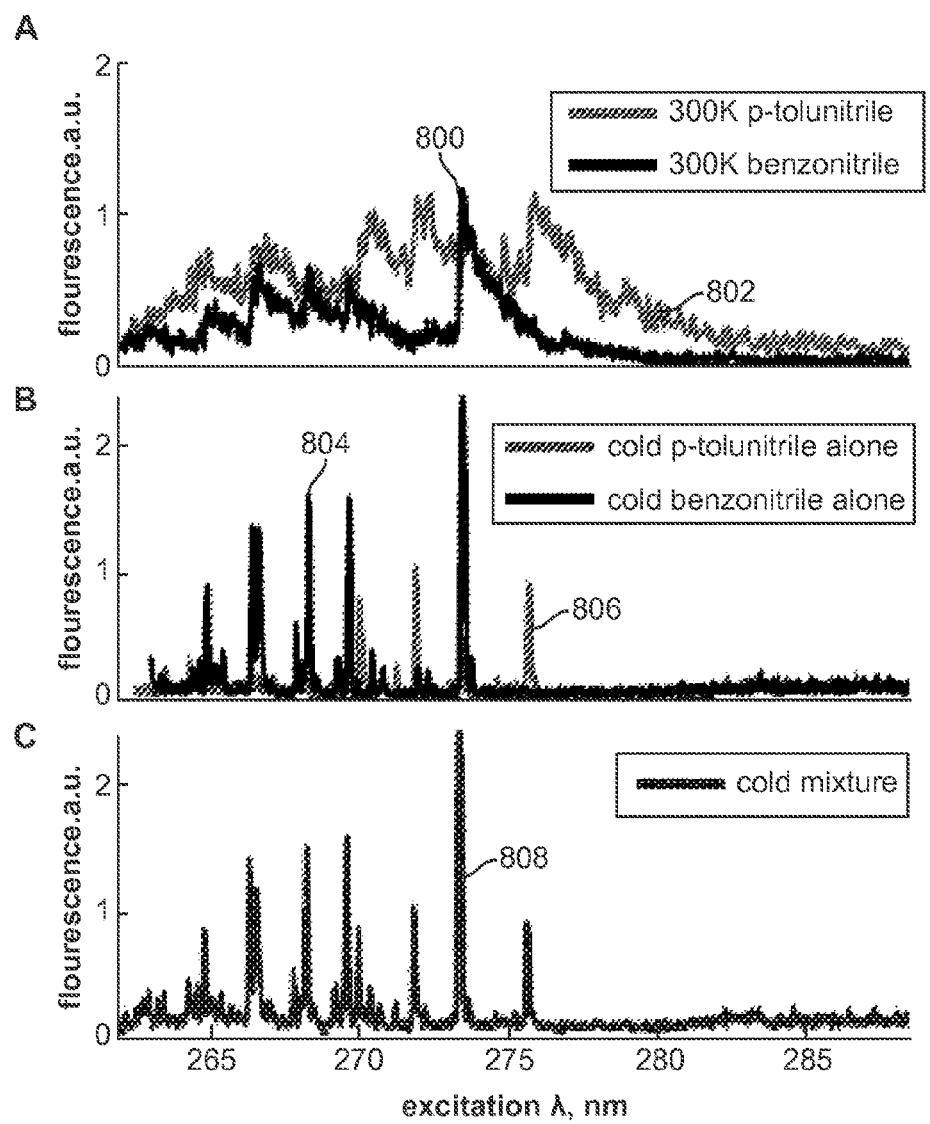
FIGS. 8A-C show experimental fluorescence spectra of p-tolunitrile and benzonitrile obtained in the system of FIG. 2, individually at 300 K (FIG. 8A), individually at cold temperature (FIG. 8B), and in a cold mixture (FIG. 8C).

Referring to FIGS. 8A-8C, in another example, buffer gas cell 200 was used to analyze a mixture of benzonitrile and p-tolunitrile. Benzontrile is a highly polar molecule (in contrast with non-polar naphthalene used in the example described above). P-tolunitrile is spectroscopically and physically similar to benzonitrile and thus presents a "challenging" case (for instance, the two molecules are not generally well resolved using UV-visible spectroscopy at room temperature).

Referring to FIG. 8A, at 300 K, the spectra of benzonitrile (curve 800) and p-tolunitrile (curve 802) are composed of generally broad features, each feature itself composed of thousands of unresolved rotational lines. Although the spectra are not identical, accurate resolution of the two spectra at room temperature is difficult. Referring to FIG. 8B, the cooled (about 40 K) spectra of benzonitrile (curve 804) and p-tolunitrile (curve 806), obtained in buffer gas cell 200, are composed of sharp peaks. Referring to FIG. 8C, it is relatively straightforward to associate peaks in the spectrum of the cold (about 40 K) mixture (curve 808), obtained in buffer gas cell 200, with individual components of the mixture. Of note, the two component species were unaffected by each other as they cooled in the mixture.

Mixture Analysis

Figure 5:
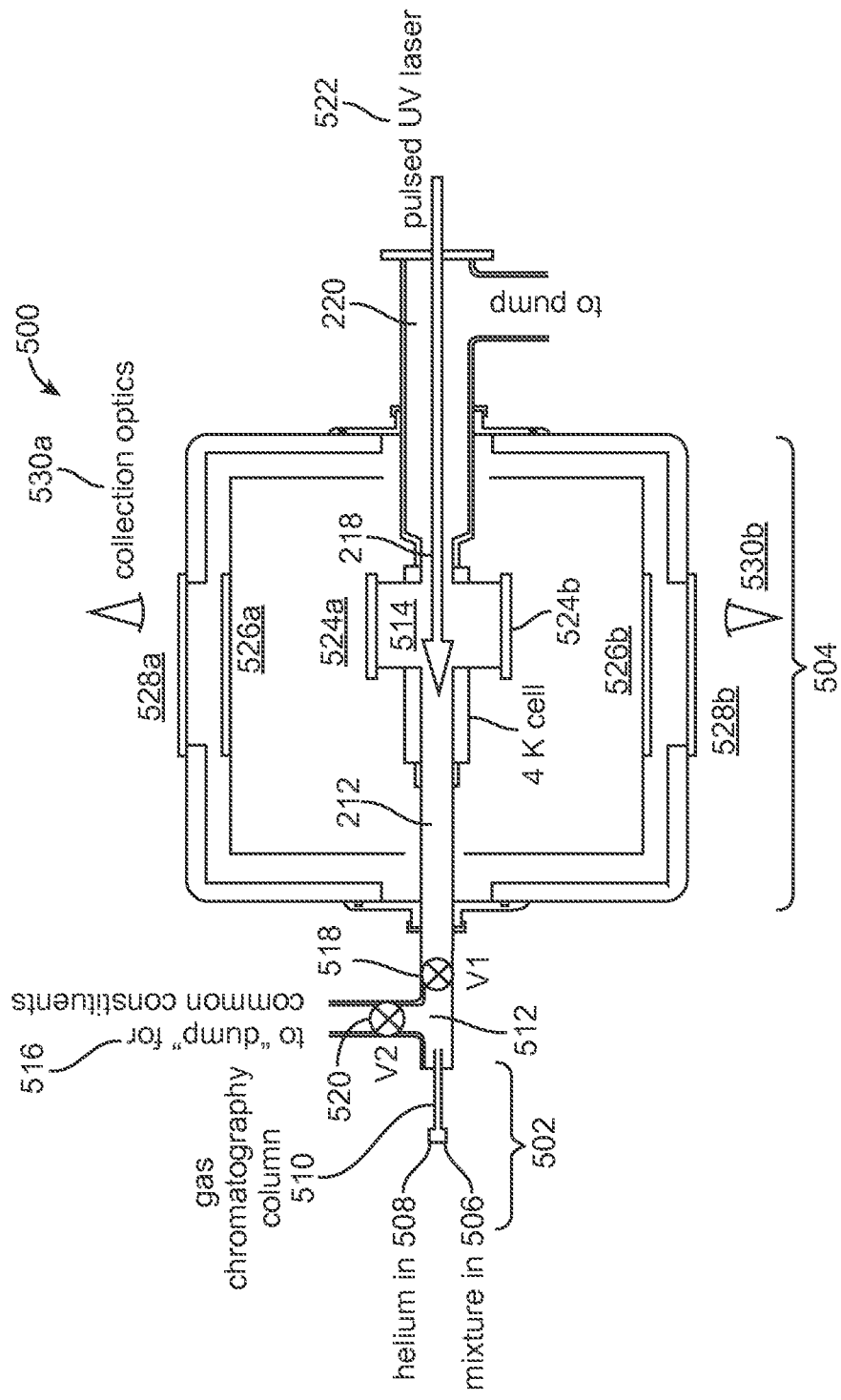
FIG. 5 is a schematic diagram of a mixture analyzer.

Referring to FIG. 5, a mixture analyzer 500 includes a capillary gas chromatograph 502 and a direct flow buffer gas cell 504. An unknown mixture of gases is loaded at atmospheric pressure and with a temperature of at least 300 K (e.g., 500 K) into a first input headspace 506 of chromatograph 502. Ultrapure helium is loaded into a second input headspace 508 of the chromatograph with a flow rate of about 20 sccm and used as the moving phase in a gas chromatography column 510. The helium bleeds the unknown gas mixture over the course of a few minutes into a receiving port 512. The initial chromatography of the unknown gas mixture coarsely separates the mixture into multiple time "channels" and separates trace components from bulk components (e.g., $N_2$ or $O_2$ in an air sample).

The separated mixture is loaded via direct gas flow into a cold cell 514, which is enabled by the ~20 sccm flow rate of the helium. When the bulk components are eluted from column 510, they can be partially or completely redirected into a dump 516 by judicious timing of valves 518 and 520, preventing gas cell 504 from being overloaded and icing up. In cold cell 514, the gas mixture is illuminated by a broadly tunable UV light source 522, such as a pulsed UV laser. The components of the mixture are detected via laser induced fluorescence as described above. The fluorescence is transmitted through quartz windows 524a, 524b on each side of cold cell tube 514, quartz windows 526a, 526b on each side of radiation shield 310, and quartz windows 528a, 528b on each side of vacuum chamber 308. The fluorescence is then collected by collection optics 530a, 530b. The collected fluorescence spectrum can be used to resolve the components of the unknown gas mixture.

Typical gas chromatographs can completely resolve a 1 $cm^3$ gas sample in a few minutes, and elute the entire gas fraction of a given chemical in about 10 seconds. Given a few second elution time and a residence time in cold cell 514 of about 0.5 seconds, the density of a given component at 4 K is about one order of magnitude lower than the density of the component in the 300 K sample, with dramatically ($10^4$ times) higher phase space density.

As an example, consider the breath of a graduate student who has recently returned from lunch. The breath contains predominantly $N_2$, $O_2$, and $CO_2$, but also contains a $10^{-11}$ fraction of monosodium glutamate (MSG), $C_5H_8NNaO_4$. 1 $cm^3$ of this breath is loaded into mixture analyzer 500 and allowed to elute through gas chromatograph 502. Over the ~1 second that the MSG is emerging from the chromatography column 510, it is accompanied by about 1 ppm air, due to imperfect separation in the column. During this second, $10^8$ MSG molecules, $10^{13}$ air molecules, and $10^{18}$ helium atoms emerge from the column. The mixture is then loaded via direct gas flow into cold cell 514, with a volume of about 10 $cm^3$ and a temperature of about 5 K. The densities in the cell are $n_{MSG}=10^7\,cm^{-3}$, $n_{air}=10^{12}\,cm^{-3}$, and $n_{He}=10^{17}\,cm^{-3}$. This mixture will not precipitate, due to the low overall contaminant density, but the MSG can be easily detected via fluorescence.

The type of light source 522 varies depending on the goals of the particular experiment. In the above example, if the user is interested only in the MSG content of the student's breath, a tunable pulsed laser may be used. For instance, a 10 GHz wide, 1 μJ pulse from such a laser tuned to an MSG absorption line will excite about 30% of the MSG molecules in cold cell 514. Collection optics 530a, 530b with a modest total efficiency of $10^{-3}$ lead to about 3000 PMT counts per pulse, easily detecting concentrations of MSG at the level of 10 parts per trillion and identifying the MSG by its unique absorption lines. Ultimate sensitivity times could be as low as $10^{-15}$.

In some cases, a tunable, narrow band, continuous wave laser may be used to resolve the rotational spectrum of the target molecule and to illuminate the sample continuously. Such lasers are in general not broadly tunable, and thus mixture analyzer 500 would need a separate light source for each substance of interest. Although there may be niche applications where this set-up is economically feasible, such an instrument would not be applicable to any generic situation.

In another embodiment, if a user wants to resolve all of the components of the target mixture, a broader, continuous light source which can be continuously scanned across the UV spectrum may be used. Examples of such a source include a monochromator that filters the output of a deuterium lamp, modern UV solid state sources (e.g., a light emitting diode, LED), an ultrafast laser, or a superradiant light source. The typical lifetime of excited molecular states is between about 100 nanoseconds and 1 μs; thus, such a light source could be scanned across as many as 10,000 channels per second. In comparison with the pulsed laser embodiment described above, this 'white light' embodiment is somewhat less sensitive (with a resolution of 100-1000 parts per trillion) due to higher scattered light; substantially (e.g., 100 times) less specific, with 1000 optical channels per GC 'elution channel' and capable of identifying mixtures with up to 500 components; faster (e.g., 1000 times); and cheaper (e.g., about 5 times).

Figure 6:
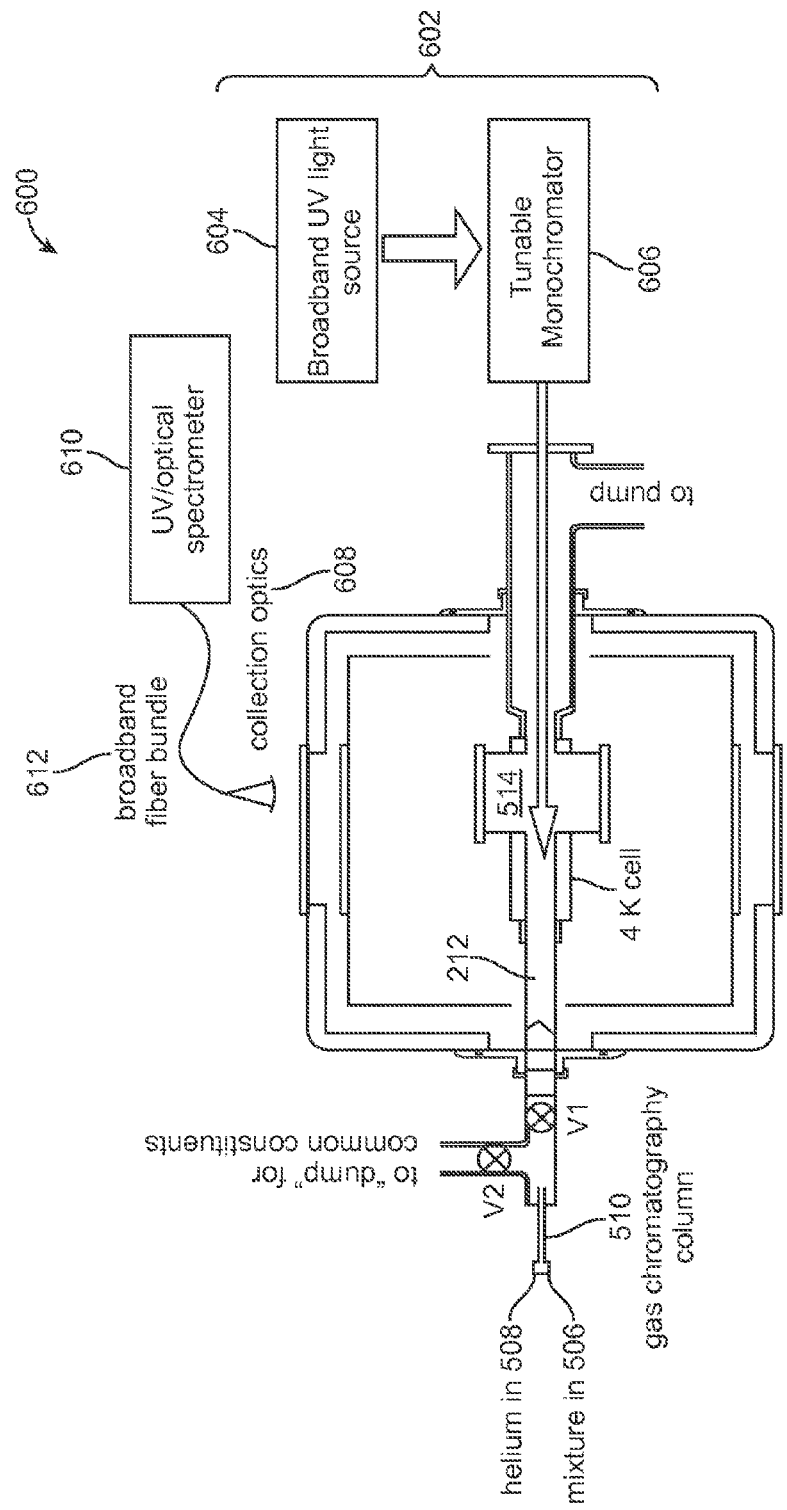
FIG. 6 is a schematic diagram of an alternative embodiment of a mixture analyzer.

Referring to FIG. 6, in another embodiment, a mixture analyzer 600 takes advantage of the fact that the emission lines as well as the absorption lines of the molecules of the cold target gas will be dramatically narrowed compared to the emission and absorption lines of room temperature molecules. Mixture analyzer 600 records both the excitation wavelength and the fluorescence spectrum of the molecules of the cold target gas. The molecules, in cold cell 514, are excited by a tunable UV light source 602, such as a combination of a broadband UV light source 604 (e.g., a deuterium lamp) and a monochromator 606. Widely tunable commercially available light sources (e.g., the Oriel Cornerstone 260¼ m Monochromator manufactured by Newport Corporation, Stratford, Conn.) have a wavelength resolution of 0.1 nm, and etalons in the monochromator can further enhance this resolution. The 0.1 nm wavelength resolution divides the UV spectrum (i.e., between 200 and 300 nm) into about 1000 channels. The fluorescence of the cold target gas is collected by collection optics 608 and transmitted to a spectrometer 610 via a broadband fiber bundle 612. Spectrometer 608 can resolve the emitted wavelength with a resolution comparable to the resolution of the monochromator (e.g., 0.11 nm). For instance, the Oriel InstaSpec X CCD system, also manufactured by Newport Corporation, may be used.

Each species in the target gas exhibits an essentially unique 'fingerprint' spectrum on a resulting ~1000×~1000 component excitation/emission matrix. In combination with relatively crude gas chromatography or cryogenic distillation, a target gas mixture with 10,000 components could be completely resolved. The sensitivity of mixture analyzer 600 is 100-1000 times lower than the sensitivity of the broadband fluorescence instrument described above because of more constrained collection optics. Additionally, mixture analyzer 600 is fairly economical, with a total component cost that may be less than, for instance, about $80,000; and mechanically robust, with no lasers or precision components. Alternate versions of mixture analyzer 600 with lower resolution and less expensive monochromators and spectrometers, and thus correspondingly lower specificity, may be constructed for even less money, such as less than $30,000.

Figure 7:
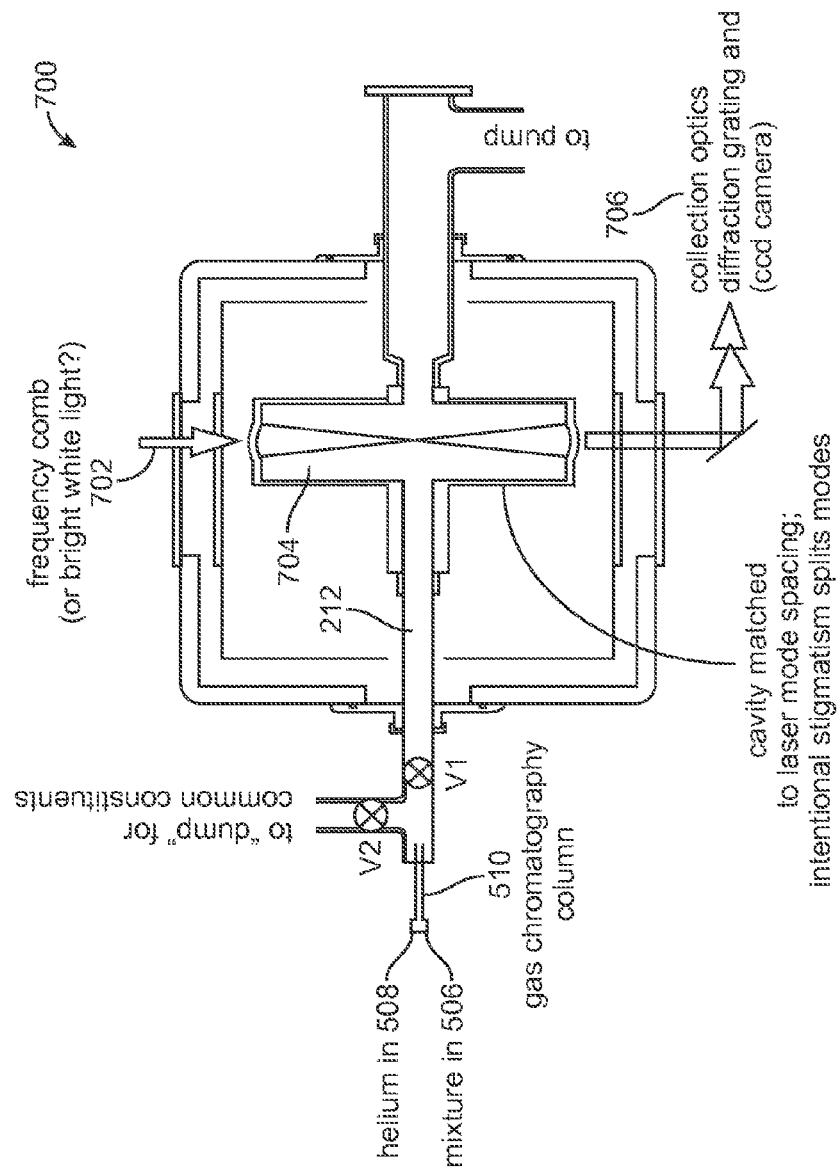
FIG. 7 is a schematic diagram of an alternative embodiment of a mixture analyzer.

Referring to FIG. 7, in another embodiment, a mixture analyzer 700 is capable of simultaneously recording a large portion of the near UV spectrum, effectively resolving complex gas mixtures at the parts per billion level in a few minutes. Mixture analyzer 700 includes a high-Q cavity absorption setup with low dispersion supermirrors. A UV frequency comb 702 provides excitation light to a cold cell cavity 704, which is matched to the mode spacing of the laser light. Intentional stigmatism in the cavity Each tooth of a frequency comb 702 is imaged by collection optics 706, such as a diffraction grating, onto a separate area of a two-dimensional CCD array via a virtual phased array (VIPA) disperser. This configuration allows the experimenter to take full advantage of high bandwidth off-the-shelf data acquisition systems developed for video acquisition. The absorption of each tooth of the comb is independently and simultaneously recorded. This system is less sensitive than a fluorescence system such as mixture analyzer 500 in FIG. 5, but is capable of analyzing the entire spectrum of the mixture at once, simultaneously resolving and identifying thousands of components of an unknown mixture. This capability is especially important when large quantities of the mixture are unavailable, as might be the case with biological samples. The confusion limit that often plagues complex mixture analysis is virtually eliminated, and the system is able to rapidly resolve fractional densities down to the 100 part per trillion range.

In mixture analyzer 700, coherence between the teeth of frequency comb 702 is not used. In an alternative embodiment, an incoherent, bright white light source is used in place of frequency comb 702. The cold cell cavity 704 'selects' the frequency of the light source, which is still imaged onto a CCD array via a VIPA spectral disperser as described above. Only a single spatial mode from the light source would be usable, and unlike comb-based spectrometers, the majority of the light would be wasted as it would not couple to a mode of the cavity. A typical 100 Watt Xenon arc lamp (e.g., Hamamatsu L10878), with an arc length of 1 mm, would result in only a tiny fraction (e.g., $10^{-8}$, or 1 µW) being coupled to the cavity. The minimal detectable absorption in the shot-noise limit scales as $\phi^{-1/2}$, which degradation would result in low sensitivity. Nevertheless, the system is much less complex than other systems described above. With a white light source, the entire system contains no component more expensive than the dewar itself, and could be assembled in its entirety for a relatively inexpensive amount of money, such as less than $50,000.

Microwave Spectroscopy

The cold gas mixture can be analyzed using microwave spectroscopy techniques. Microwave spectroscopy would be considerably less expensive than optical spectroscopy, but also substantially less sensitive.

In some implementations, pulsed Fourier Transform Microwave (FTMW) Spectroscopy (also known as free induction decay detection) is used. Specifically, analyte molecules in buffer gas cell 200 are allowed to thermalize with a buffer gas such that more molecules are in the lower state than are in the upper state of any given transition.

The molecules are polarized by a short, strong microwave pulse. The pulse (e.g., a π/2 pulse) leaves the molecules in a superposition of the lower and higher rotational states. This coherent superposition of states gives the gas in buffer gas cell 200 a macroscopic oscillating electric dipole moment.

The pulse is then turned off and the gas radiates at unique, characteristic frequencies. These frequencies, which are set by the rotational moments of inertia of the molecules therein, are essentially unique to each molecule. The radiation of the gas is amplified and digitized; the Fourier transform of the radiation signal contains peaks at the characteristic frequencies of each molecule in the gas mixture.

After the analyte molecules have undergone a small number (e.g., approximately 1) of collisions with the buffer gas, the analyte molecules are depolarized, returning them to thermal equilibrium. At this point, the excitation and detection process can be repeated.

Under typical buffer gas cooling conditions, the detection process described above takes, e.g., a few microseconds, and can be repeated rapidly (e.g., 100 kHz or faster). The actual measured signal may be the accumulated average of these repetitions.

In some examples, synthesizers and digitizers are used that allow for an entire microwave spectrum to be recorded simultaneously, further increasing sensitivity per unit time.

The use of microwave spectroscopy techniques in conjunction with buffer gas cell 200 has a number of advantages. Because microwaves are detected coherently, accurate and exact frequency measurements are enabled, and the simultaneous detection of and discrimination between many distinct frequencies is possible. Furthermore, because of the coherent emission of microwaves, the signal from many analyte molecules may be used, resulting in a greatly enhanced radiation rate as compared to a single molecule. Specifically, radiated power in microwave spectroscopy generally scales as $n^2$, where n is the density of the gas; by comparison, radiated power in optical spectroscopy generally scales linearly with n. Thus, cooling an analyte gas, e.g., in buffer gas cell 200, results in even greater gains for microwave spectroscopy than for optical spectroscopy. Additionally, microwave technology is well-developed, relatively inexpensive, and reliable.

Because only polar molecules have observable pure rotational lines, a microwave detector is blind to non-polar molecules. In some embodiments, in order to observe polar molecules, a noble gas atom (e.g., Ne, Kr, or Xe) is adhered to the molecule, resulting in a polar complex that is detectable by FTMW spectroscopy.

The sensitivity of microwave spectroscopy utilized with buffer gas cell 200 is generally in the range of parts per billion using room temperature microwave components. In some embodiments, the use of cryogenic amplifiers may increase the sensitivity of the system.

Alternative Embodiments

In an alternative implementation, a broadband infrared light source is used to excite the gas in the cold cell tube, enabling Fourier Transform Infrared (FTIR) scanning absorption techniques to be utilized.

While there are no specific size restrictions on the molecules that can be uniquely resolved using the above described direct flow loading methods and systems, there are general criteria for the molecules. In order to cool efficiently, molecules are preferably larger than helium in order to satisfy the constraint that $\sigma_{A-He} > \sigma_{He-He}$. Such a constraint is certainly satisfied for molecules of comparable size or larger than naphthalene and may be met even for rather small molecules such as ammonia ($NH_3$). The cooled target species also preferably remains free of adsorbed helium atoms, which is likely to be the case for molecules with less than about 40 atoms, although the geometry of the molecule also plays a factor in helium adsorption. Pheromones, which generally have about 50 atoms, are difficult to resolve, and molecules much larger or more flexible than pheromones may also be difficult.

The spectrometers described above could be useful even if each molecule of analyte was covered with a layer of adsorbed helium atoms. The random configurations of the helium atoms would broaden each transition by a few $cm^{-1}$, effectively precluding the resolution of rotational lines. The spectrometer would nevertheless resolve the UV absorption spectrum from 200-400 nm into over 25,000 independent channels, allowing for excellent discrimination between even rather large molecules. As another alternative, the analyzer could be run at higher temperatures. For instance, operating at 15-20 K would produce significant narrowing of spectral features compared to a 300 K vapor, but even in equilibrium almost no helium would be adsorbed onto the molecules. The monochromator-based element of FIG. 6 would likely not be affected at all by this heating.

In some embodiments, the gas chromatography column is replaced with a cryogenic plate, held at a temperature low enough to condense most 'interesting' molecules but high enough not to condense majority constituents such as air. The plate is then gradually warmed, releasing the condensed molecules into the helium flow, which sweeps the molecules rapidly into the much colder buffer gas cell while keeping them in the gas phase. The use of a cryogenic plate can in principle greatly increase sensitivity as trace components can be enormously concentrated in such a cold trap.

The methods and systems described above for large molecule injection can be combined with buffer-gas beam methods to produce cold, slow beams of large molecules, which are useful for, e.g., ultraprecise spectroscopic applications. The pumping line (e.g., pumping line 220 in FIG. 2) is with a flat nozzle connected to a cryopumped vacuum so that a species of interest can be separated from the buffer gas via optical, electric, or magnetic fields. Such a configuration produces a continuous, cold, high flux ($3\times10^{14}$ molecules/second) beam of naphthalene, or another similar sized molecule, in high vacuum. The beam would have a forward velocity of about 150 m/s. These techniques are extendable to larger polar molecules such as benzonitrile ($C_6H_5CN$, 4.2 Debye) or azulene, a polar isomer of naphthalene ($C_{10}H_8$, 0.8 Debye). Such a beam of larger polar molecules would make an attractive source for alternating gradient decelerators.

The cooling methods and systems described above can also be used as a tool for investigating cold chemistry, such as cold gas-phase chemical reaction rates. Cold chemistry is relevant for, e.g., chemistry in the interstellar medium, spin and orientation mediated chemical reactions, and field mediated reactions. The high densities, long interaction times (up to 50 ms in the current system), and generality of the cooling techniques described herein allow for a large variety of experiments, ranging from exploration of three body recombination to the possibility of field mediated reactions of aligned polar molecules. Such cooling techniques also enable the measurement of low temperature recombination rates.

Additional description of methods and systems for cooling and detection of gas mixtures is included in the attached 13-page Appendix entitled "Cooling and Collisions of Large Gas Phase Molecules."

It is to be understood that the foregoing description is intended to illustrate and not to limit the scope of the invention, which is defined by the scope of the appended claims. Other embodiments are within the scope of the following claims.

What is claimed is:

1. A system comprising:
a cold cell tube configured to receive a mixture of a target gas and a buffer gas to cool the target gas to a temperature at which a partial pressure of the target gas is greater than the saturated vapor pressure of the target gas while maintaining at least a portion of the target gas in the gas phase;
a spectroscopic module configured to detect the cooled target gas in the cold cell tube; and
an analysis module configured to determine a characteristic of the target gas based on the results of the detecting.

2. The system of claim 1, wherein the target gas includes a plurality of chemical species and the characteristic of the target gas includes an identity of at least one of the chemical species.

3. The system of claim 2, wherein the cold cell tube is configured to cool the target gas to a temperature at which a partial pressure of each chemical species is greater than the saturated vapor pressure of that chemical species.

4. The system of claim 2, wherein, for at least one of the chemical species included in the target gas, an elastic scattering cross section between a molecule of the at least one chemical species and a molecule of the buffer gas is greater than an elastic scattering cross section between a first molecule of the buffer gas and a second molecule of the buffer gas.

5. The system of claim 1, wherein the cold cell tube is configured to increase a phase space density of the target gas.

6. The system of claim 1, wherein the cold cell tube is configured to cool the target gas to a temperature at which single vibrational lines of the target gas are spectroscopically resolvable by the spectroscopic module.

7. The system of claim 1, further comprising:
an input module configured to receive the mixture of the target gas and the buffer gas; and
a transition tube disposed between the input module and the cold cell tube.

8. The system of claim 7, wherein the input module includes a capillary gas chromatograph configured to receive the mixture of the target gas and the buffer gas.

9. The system of claim 7, wherein the input module includes a cryogenic plate configured to condense at least some components of the target gas.

10. The system of claim 9, further comprising:
a heating element configured to heat the cryogenic plate, wherein, when the cryogenic plate is heated, at least some components of the target gas are released to the transition tube.

11. The system of claim 1, wherein the spectroscopic module comprises:
a light source configured to excite the cooled target gas; and
an emissions detector configured to detect at least one of a fluorescence emitted by at least one component of the target gas in response to the excitation and an absorption by at least one component of the target gas in response to the excitation.

12. The system of claim 11, wherein the light source includes a tunable laser configured to emit light at a wavelength capable of exciting the fluorescence of at least one component of the target gas.

13. The system of claim 11, wherein the light source includes a light source configured to emit a plurality of wavelengths; and a monochromator.

14. The system of claim 1, wherein the spectroscopic module comprises:
a microwave source configured to excite the cooled target gas; and
a microwave detector configured to detect at least one of absorption or emission of microwaves by at least one component of the target gas in response to the excitation.

15. The system of claim 1, wherein the spectroscopic module comprises:
a broadband infrared light source configured to excite the cooled target gas; and
a detector configured to detect an absorption by at least one component of the target gas in response to the excitation according to Fourier Transform Infrared (FTIR) scanning absorption.

16. The system of claim 1, wherein the cold cell tube is configured to cool the target gas without substantially changing a density of the target gas.

17. A method comprising:
receiving a mixture of a target gas and a buffer gas;
cooling the target gas to a temperature at which a partial pressure of the target gas is greater than the saturated vapor pressure of the target gas while maintaining at least a portion of the target gas in the gas phase;
spectroscopically detecting the cooled target gas; and
determining a characteristic of the target gas based on the results of the detecting.

18. The method of claim 17, wherein the target gas includes a plurality of different chemical species and wherein determining a characteristic of the target gas includes identifying at least one of the chemical species.

19. The method of claim 18, wherein cooling the target gas includes cooling the target gas to a temperature at which a partial pressure of each chemical species is greater than the saturated vapor pressure of that chemical species.

20. The method of claim 18, wherein, for at least one of the chemical species included in the target gas, an elastic scattering cross section between a molecule of the at least one chemical species and a molecule of the buffer gas is greater than an elastic scattering cross section between a first molecule of the buffer gas and a second molecule of the buffer gas.

21. The method of claim 17, wherein cooling the target gas includes increasing a phase space density of the target gas.

22. The method of claim 17, wherein cooling the gas includes cooling the gas to a temperature at which single vibrational lines of the target gas are spectroscopically resolvable.

23. The method of claim 17, further comprising receiving the mixture of the target gas and the buffer gas in an input module.

24. The method of claim 23, wherein receiving the mixture in the input module includes receiving the mixture of the target gas and the buffer gas in a capillary gas chromatograph.

25. The method of claim 23, wherein receiving the mixture in the input module includes condensing at least some components of the target gas on a cryogenic plate.

26. The method of claim 25, further comprising heating the cryogenic plate, wherein, when the cryogenic plate is heated, at least some components of the target gas are released.

27. The method of claim 17, wherein spectroscopically detecting the cooled target gas includes optically detecting the cooled target gas.

28. The method of claim 27, wherein optically detecting the target gas includes:

exciting the target gas using a light source; and detecting at least one of a fluorescence emitted by at least one component of the target gas in response to the excitation and an absorption by at least one component of the target gas in response to the excitation.

29. The method of claim 17, wherein spectroscopically detecting the cooled target gas includes:

exciting the target gas using a microwave source; and detecting at least one of absorption or emission of microwaves by at least one component of the target gas in response to the excitation.

30. The method of claim 29, wherein spectroscopically detecting the cooled target gas includes detecting the cooled target gas using pulsed Fourier Transform Microwave Spectroscopy.

31. The method of claim 17, wherein cooling the target gas includes cooling the target gas without substantially changing a density of the target gas.

* * * * *